United States Patent
Kim et al.

(10) Patent No.: US 10,386,348 B2
(45) Date of Patent: Aug. 20, 2019

(54) OLFACTORY SENSING DEVICE AND METHOD FOR MEASURING ODOR

(71) Applicant: Samsung Electronics Co., Ltd., Gyeonggi-do (KR)

(72) Inventors: Tae-Pyeong Kim, Gyeonggi-do (KR); Si-Hoon Lee, Gyeonggi-do (KR); Farah Alnaimi, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 389 days.

(21) Appl. No.: 14/698,513

(22) Filed: Apr. 28, 2015

(65) Prior Publication Data
US 2015/0308996 A1    Oct. 29, 2015

(30) Foreign Application Priority Data

Apr. 28, 2014 (KR) .................. 10-2014-0050802

(51) Int. Cl.
*G01N 33/00* (2006.01)
(52) U.S. Cl.
CPC ................. *G01N 33/0001* (2013.01)
(58) Field of Classification Search
None
See application file for complete search history.

(56) References Cited

U.S. PATENT DOCUMENTS

| 8,933,706 | B1* | 1/2015 | Karlquist | G01J 5/44 324/633 |
| 2006/0001329 | A1* | 1/2006 | Rao | H03H 9/02102 310/315 |
| 2006/0222568 | A1* | 10/2006 | Wang | B82Y 15/00 422/70 |
| 2006/0232163 | A1* | 10/2006 | Rudy | G01K 11/265 310/319 |
| 2007/0000305 | A1* | 1/2007 | Ma | G01N 29/022 73/24.01 |
| 2007/0176705 | A1* | 8/2007 | Sutardja | H01L 23/34 331/176 |
| 2008/0230859 | A1* | 9/2008 | Zaghloul | G01N 29/022 257/428 |

(Continued)

FOREIGN PATENT DOCUMENTS

| KR | 10-0876158 | 12/2008 |
| WO | WO 2013/137867 | 9/2013 |

OTHER PUBLICATIONS

Rai, S., Ying Su, Wei Pang, R. Ruby, and B. Otis. "A Digitally Compensated 1.5 GHz CMOS/FBAR Frequency Reference." IEEE Transactions on Ultrasonics, Ferroelectrics and Frequency Control 57.3 (2010): 552-61.*

(Continued)

*Primary Examiner* — J. E. Schoenholtz
(74) *Attorney, Agent, or Firm* — The Farrell Law Firm, P.C.

(57) ABSTRACT

A method for measuring an odor in an olfactory sensing device is provided. The method includes sensing an odor using at least one odor sensor, estimating a current temperature using a temperature count coefficient of a monitor sensor, calculating an odor count coefficient variation for the at least one sensor, and measuring the odor by applying a temperature count coefficient variation corresponding to a temperature change to the odor count coefficient variation.

4 Claims, 5 Drawing Sheets

(56) References Cited

U.S. PATENT DOCUMENTS

| | | | |
|---|---|---|---|
| 2009/0146746 A1 | 6/2009 | Unkrich et al. | |
| 2012/0290222 A1 | 11/2012 | Inoue et al. | |
| 2013/0093468 A1* | 4/2013 | Rebel | H03K 23/66 327/105 |
| 2015/0013461 A1* | 1/2015 | Pollard | H01L 41/1132 73/579 |

OTHER PUBLICATIONS

S. Rai, Y. Su, A. Dobos, R. Kim, W. Pang, R. Ruby, and B. Otis, "A 1.5 GHz Temperature Stable CMOS/FBAR Frequency Reference," in International Frequency Control Symposium (FCS), 2009. IEEE, Jun. 2009.*

Rai, Shailesh, Ying Su, Aron Dobos, Richard Kim, Richard Ruby, Wei Pang, and Brian Otis. "A 1.5GHz CMOS/FBAR Frequency Reference with ±10ppm Temperature Stability." 2009 IEEE International Frequency Control Symposium Joint with the 22nd European Frequency and Time Forum (2009).*

Nagaraju, Manohar, Jingren Gu, Andrew Lingley, Fan Zhang, Martha Small, Richard Ruby, and Brian Otis. "A Fully Integrated Wafer-scale Sub-mm3 FBAR-based Wireless Mass Sensor." 2014 IEEE International Frequency Control Symposium (FCS) (2014).*

Johnston, Matthew L., Hassan Edrees, Ioannis Kymissis, and Kenneth L. Shepard. "Integrated VOC Vapor Sensing on FBAR-CMOS Array." 2012 IEEE 25th International Conference on Micro Electro Mechanical Systems (MEMS) (2012).*

"RF Frequency Counter" Apr. 5, 2014, downloaded from URL<https://web.archive.org/web/20140405005558/http://www.radio-electronics.com/info/t_and_m/frequency_counter/counter_basics.php> on Jul. 25, 2017.*

Samsung's New Quad-Core Application Processor Drives Advanced Feature Sets in Smartphones and Tablets Apr. 26, 2012 downloaded from URL<. https://news.samsung.com/global/samsung%E2%80%99s-new-quad-core-application-processor-drives-advanced-feature-sets-in-smartphones-and-tablets> on Jul. 21, 2017.*

Johnston, M.L., "Thin film Bulks Acoustic Resonators on Integrated Circuits for Physical Sensing Applications". Diss. Columbia University 2012.*

Mathias Link, Study and realization of shear wave mode solidly mounted film bulk acoustic resonators (FBAR) made of c-axis inclined zinc oxide (ZnO) thin films: application as gravimetric sensors in liquid environments. Mechanics [physics.med-ph]. Université Henri Poincaré—Nancy I, 2006. English. <tel-00110411>.*

Johnston, M.L., "Thin film Bulks Acoustic Resonators on Integrated Circuits for Physical Sensing Applications". Diss. Columbia University 2012. (Year: 2012).*

* cited by examiner

OLFACTORY SENSING DEVICE AND METHOD FOR MEASURING ODOR

PRIORITY

This application claims priority under 35 U.S.C. § 119(a) to a Korean Patent Application filed in the Korean Intellectual Property Office on Apr. 28, 2014, and assigned Serial No. 10-2014-0050802, the entire disclosure of which is incorporated herein by reference.

BACKGROUND

1. Field of Invention

The present invention relates generally to an olfactory sensing device and method for measuring an odor.

2. Description of Related Art

In general, it is possible to identify chemical species existing in the gas phase using devices such as gas chromatography or mass spectrograph. In recent years, many studies have been performed to analyze chemical species using a mobile terminal. In order to increase the utility value of the mobile terminal, various applications executable in the mobile terminal have been developed to interact with an olfactory sensing device which may be mounted through an external interface of the mobile terminal to measure an odor.

In the conventional olfactory sensing device, a temperature sensor may be additionally mounted to perform a correction for any environmental changes. Alternatively, an enclosed space may be used to measure an odor.

However, due to the additional mounting of the temperature sensor, the conventional olfactory sensing device may increase in the cost and mounting area, causing an increase in the price and size of the mobile device. In addition, the enclosed space where the conventional olfactory sensing device measures an odor may be different from the place where the product is actually used, making it difficult to ensure the mass production.

Therefore, there is a need for an olfactory sensing device that can determine the amount of odor molecules by correcting for changes in the external environment, such as temperature changes, using existing sensors instead of a separate device for measuring the temperature.

SUMMARY

The present invention has been made to address at least the problems and disadvantages described above, and to provide at least the advantages described below.

Accordingly, an aspect of the present invention is to provide an olfactory sensing device and method for measuring an odor.

In accordance with an aspect of the present invention, there is provided a method for measuring an odor in an olfactory sensing device. The method includes sensing an odor using at least one odor sensor, estimating a current temperature using a temperature count coefficient of a monitor sensor, calculating an odor count coefficient variation for the at least one odor sensor, and measuring the odor by applying a temperature count coefficient variation corresponding to a temperature change to the odor count coefficient variation.

In accordance with another aspect of the present invention, there is provided an olfactory sensing device for measuring an odor. The device includes a sensing unit including at least one odor sensor that senses an odor, and a controller which estimates a current temperature using a temperature count coefficient of a monitor sensor, calculates an odor count coefficient variation for the at least one odor sensor, and measures the odor by applying a temperature count coefficient variation corresponding to a temperature change to the odor count coefficient variation.

In accordance with further another aspect of the present invention, there is provided a non-transitory computer-readable storage medium having stored thereon a program including instructions to measure an odor in an olfactory sensing device. The instructions include the steps of sensing an odor using at least one odor sensor, estimating a current temperature using a temperature count coefficient of a monitor sensor, calculating an odor count coefficient variation for the at least one odor sensor, and measuring the odor by applying a temperature count coefficient variation corresponding to a temperature change to the odor count coefficient variation.

BRIEF DESCRIPTION OF THE DRAWINGS

The above and other aspects, features and advantages of the present invention will be more apparent from the following detailed description taken in conjunction with the accompanying drawings, in which.

DETAILED DESCRIPTION OF EMBODIMENTS OF THE PRESENT INVENTION

Hereinafter, embodiments of the present invention are described with reference to the accompanying drawings. Various changes may be made to the present invention, and the present invention may come with various embodiments. Some embodiments of the present invention are shown and described in connection with the drawings. However, it should be appreciated that the present invention is not limited to the embodiments disclosed herein. All changes and/or equivalents or replacements thereto also belong to the scope of the present invention.

The same or similar reference numerals are used to refer to the same or similar elements throughout the specification and the drawings.

The terms "comprise" and/or "comprising", as used herein, specify the presence of disclosed functions, operations, or components, but do not preclude the presence or addition of one or more other functions, operations, or components. It will be further understood that the terms "comprise" and/or "have," when used in this disclosure, specify the presence of stated features, integers, steps, operations, elements, and/or components, but do not preclude the presence or addition of one or more other features, integers, steps, operations, elements, components, and/or groups thereof.

As used herein, the terms "A or B" or "at least one of A and/or B" include any and all combinations of one or more of the associated listed items. For examples, "A or B" or "at least one of A or/and B" each may include A, or include B, or include both A and B.

Ordinal numbers as herein used, such as "first", "second", etc., may modify various components of various embodiments, but do not limit those components. For example, these terms do not limit the order and/or importance of the components. These terms are only used to distinguish one component from another. For example, a first user device and a second user device are different user devices from each other. For example, according to various embodiments of the present invention, a first component may be referred to as a second component, and vice versa without departing from the scope of the present invention.

When a component is "connected to" or "coupled to" another component, the component may be directly connected or coupled to the other component, or one or more other components may intervene between the two components. In contrast, when a component is "directly connected to" or "directly coupled to" another component, no other intervening components may intervene between the two components.

It is to be understood that the singular forms "a," "an," and "the" include plural references unless the context clearly dictates otherwise.

The terms as used herein are provided merely to describe the embodiments described herein, but not to limit the present invention. Unless otherwise defined, all terms including technical and scientific terms used herein have the same meaning as commonly understood by one of ordinary skill in the art to which the embodiments of the present invention belong. It will be further understood that terms, such as those defined in commonly used dictionaries, should be interpreted as having meanings consistent with their meanings in the context of the relevant art and should not be interpreted in an idealized or overly formal sense, unless expressly so defined herein.

An electronic device according to the present invention is a device with a function for measuring an odor corresponding to a temperature change. For example, the electronic device may be at least one of a smart phone, a tablet Personal Computer (PC), a mobile phone, a video phone, an e-book reader, a desktop PC, a laptop PC, a Netbook computer, a Personal Digital Assistant (PDA), a Portable Multimedia Player (PMP), an MP3 player, a mobile medical device, a camera or a wearable device (e.g., a Head-Mounted-Device (HMD) (such as electronic glasses), electronic apparel, an electronic bracelet, an electronic necklace, an electronic accessory (appcessory), an electronic tattoo, or a smart watch), or may be an electronic device that can be connected to these various electronic devices.

In some embodiments, the electronic device may be a smart home appliance with a function for measuring an odor corresponding to the temperature change. The smart home appliance, for example, the electronic device, may include at least one of a television (TV), a Digital Versatile Disc (DVD) player, an audio set, a refrigerator, an air conditioner, a cleaner, an oven, a microwave, a washer, an air purifier, a set-top box, a TV box (e.g., Samsung HomeSync™, Apple TV™, or Google TV™), a game console, an electronic dictionary, an electronic key, a camcorder, or an electronic photo frame.

In some embodiments, the electronic device may include at least one of part of furniture or building/structure, an electronic board, an electronic signature receiving device, a projector or various meters (e.g., water, electricity, gas or radio meters), each of which has a function for measuring an odor.

The electronic device according to the present invention may be one of the above-described devices or a combination thereof. In addition, the electronic device according to the present invention may be a flexible device. It will be apparent to those of ordinary skill in the art that the electronic device according to the present invention is not limited to the above-described devices.

An electronic device according to various embodiments will now be described with reference to the accompanying drawings. The term 'user', as used in the description of the various embodiments, may refer to a person who uses the electronic device, or a device (e.g., an intelligent electronic device) that uses the electronic device.

Figure 1:
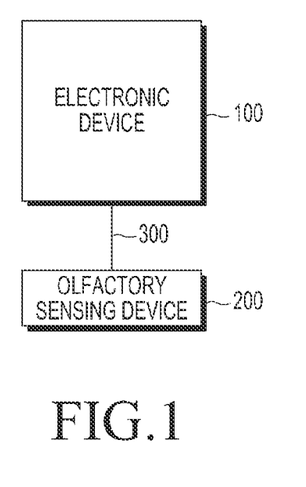
FIG. 1 is a block diagram illustrating a system for sensing an odor, according to an embodiment of the present invention.

FIG. 1 is a block diagram illustrating a system for sensing an odor, according to an embodiment of the present invention.

Referring to FIG. 1, the system for sensing an odor includes an electronic device 100 and an olfactory sensing device 200. The electronic device 100 and the olfactory sensing device 200 are connected to each other in a wired or wireless manner, as shown by reference numeral 300.

The olfactory sensing device 200 has a function for sensing or measuring an odor, and is an accessory connected to the electronic device 100. The olfactory sensing device 200 is equipped with various interfaces, depending on the type and manufacturer of the electronic device 100, to perform mutual communication with the electronic device 100.

The olfactory sensing device 200 is connected to the electronic device 100 through at least one of a Universal Serial Bus (USB), a High-Definition Multimedia Interface (HDMI) and a Mobile Industry Processor Interface (MIPI), or through a wired/wireless communication protocol.

As described herein, the olfactory sensing device 200 for measuring odors is configured separately from the electronic device 100 and connected thereto through an interface; however this is only an example.

When the olfactory sensing device 200 is connected to electronic device 100, the electronic device 100 senses various odors by analyzing the air particles to identify an odor or toxic chemicals. The electronic device 100 includes at least one module for measuring these various odors.

Upon detecting a connection to the olfactory sensing device 200, the electronic device 100 sends a command to the olfactory sensing device 200 to measure an odor. In addition, the electronic device 100 receives data including information about an odor measured by the olfactory sensing device 200, analyzes the received data, and transmits the analyzed data to another electronic device, or displays the analyzed data on a screen.

The olfactory sensing device 200 detects connection that is made not only through USB, HDMI or MIPI, but also through a wired cable capable of transmitting/receiving data through a connection, or an interface that is based on a protocol for wireless communication.

The olfactory sensing device 200 receives a command to measure or sense an odor from the electronic device 100 through these various interfaces.

Upon detecting its connection to the electronic device 100 and receiving a command to measure an odor from the electronic device 100, the olfactory sensing device 200 senses an odor using at least one odor sensor, estimates the current temperature using a count coefficient of a monitor sensor, calculates an odor count coefficient variation for the odor sensor that has sensed the odor, and applies a temperature count coefficient variation corresponding to a temperature change, to the calculated odor count coefficient variation, to measure the odor.

The olfactory sensing device 200 calculates an odor count coefficient variation by identifying the odor count coefficient for the odor sensor that has sensed an odor, and compares the identified odor count coefficient with a pre-stored odor count coefficient of the sensor that has sensed the odor. The pre-stored odor count coefficient may be stored in a table.

The olfactory sensing device 200 measures an odor by subtracting a temperature count coefficient variation, which corresponds to a temperature change, from the calculated odor count coefficient variation. The temperature change corresponds to a difference between the estimated current temperature and a reference temperature in the table.

The olfactory sensing device 200 determines the sensed odor based on the subtracted coefficient, and updates the subtraction result in the table. The table includes an odor count coefficient for determining an odor sensed by each of at least one odor sensor corresponding to the temperature and a temperature count coefficient of a monitor sensor corresponding to the temperature.

The odor count coefficient is a value obtained by converting a resonant frequency of the sensor, which is changed depending on the molecules of the sensed odor, into a digital value. The sensor may include a Film Bulk Acoustic Resonator (FBAR), and may be doped with a receptor to measure an odor. The temperature count coefficient of the monitor sensor may be pre-stored in a storage unit.

Figure 2:
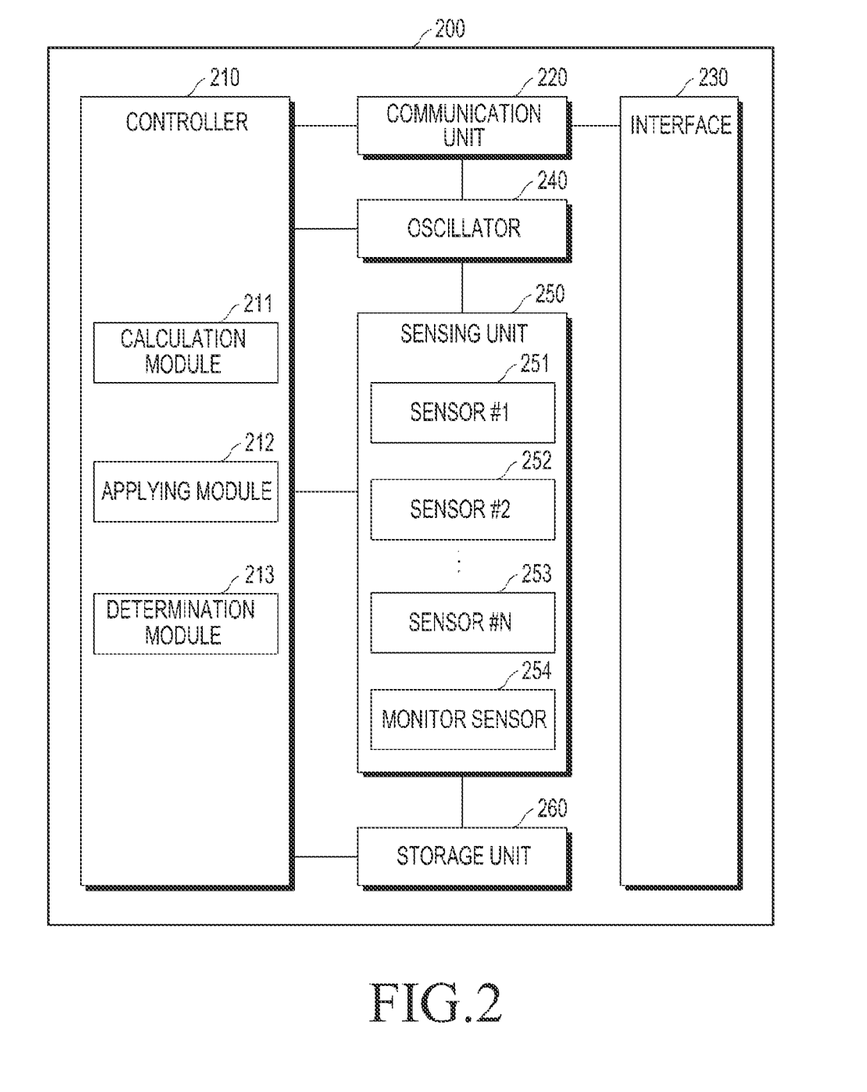
FIG. 2 is a block diagram illustrating an olfactory sensing device for measuring an odor, according to an embodiment of the present invention.

FIG. 2 is a block diagram illustrating an olfactory sensing device for measuring an odor, according to an embodiment of the present invention.

Referring to FIG. 2, the olfactory sensing device 200 for measuring an odor includes a controller 210, a communication unit 220, an interface 230, an oscillator 240, a sensing unit 250, and a storage unit 260. Each of the controller 210, the communication unit 220, the interface 230, the oscillator 240, the sensing unit 250, and the storage unit 260 delivers a signal or data through a bus.

In the olfactory sensing device 200 for measuring an odor, the functions performed by controller 210, the communication unit 220, the interface 230, the oscillator 240, the sensing unit 250, and the storage unit 260 may be configured separately for each function, or all the functions performed in the olfactory sensing device 200 may be configured on a single chip.

The communication unit 220 connects communication between the olfactory sensing device 200 and the electronic device 100. For example, the communication unit 220 communicates with the electronic device 100 by accessing a network through wireless communication or wired communication.

The wireless communication includes at least one of, for example, WiFi, Bluetooth (BT), Near Field Communication (NFC), Global Positioning System (GPS) or cellular communication (e.g., Long Term Evolution (LTE), Long Term Evolution Advanced (LTE-A), Code Division Multiple Access (CDMA), Wideband Code Division Multiple Access (WCDMA), Universal Mobile Telecommunication System (UMTS), Wireless Broadband (WiBro), Global System for Mobile communication (GSM) or the like).

The wired communication includes at least one of, for example, USB, HDMI, Recommended Standard 232 (RS-232) or Plain Old Telephone Service (POTS).

The interface 230, which is an input/output device for performing communication with at least one electronic device, outputs or receives a command externally. In addition, the interface 230 transmits the received command, data, or signal to the controller 210 through the communication unit 220. The interface 230 delivers the data received from the electronic device 100 to the controller 210 through the communication unit 220, and transmits the signal or data received through the communication unit 220 to the electronic device 100.

The oscillator 240 outputs a clock that is used to measure an odor. The oscillator 240 includes a Pierce oscillator that is made by connecting a piezoelectric crystal between a collector and a base of an emitter grounded transistor. At least one or more odor sensors 251, 252 and 253 of the sensing unit 250 measures an odor at predetermined intervals in the output clock.

The sensing unit 250 senses or measures the ambient odor using the at least one odor sensor. The sensing unit 250 includes at least one or more odor sensors 251, 252, and 253 for sensing the odor. In addition, the sensing unit 250 includes a monitor sensor 254 for estimating the temperature. According to an embodiment of the present invention, the sensing unit 250 may include multiple monitor sensors for estimating the temperature.

The one or more odor sensors 251, 252, and 253 may include an FBAR, and may be doped with a receptor to measure an odor. The one or more odor sensors 251, 252, and 253 may be provided in the sensing unit 250, or in the oscillator 240.

The sensing unit 250 repeatedly performs an operation of sensing an odor and pausing (or waiting for) an odor sensing at predetermined periods of a clock output from the oscillator 240. The sensing unit 250 delivers information about the sensed odor to the controller 210, and the controller 210 generates data to be transmitted to the electronic device 100, using the sensing result from the sensing unit 250. The sensing unit 250 switches an operating state of the one or more odor sensors 251, 252, and 253 to an idle state if a new clock is generated, and after the lapse of a predetermined time, the sensing unit 250 activates the one or more odor sensors 251, 252, and 253 to sense an odor.

The one or more odor sensors 251, 252, and 253 may be provided inside or outside the olfactory sensing device 200, and may be provided in any position of the olfactory sensing device 200. The olfactory sensing device 200 senses an odor using the activated one or more odor sensors 251, 252, and 253 for a predetermined time, and after a lapse of the predetermined time, the olfactory sensing device 200 pauses the odor sensing and switches the operating state of the one or more odor sensors 251, 252, and 253 to a waiting state. The sensing unit 250 repeatedly performs the operation of odor sensing and waiting, and delivers the operation result to the controller 210.

The storage unit 260 stores a table that includes an odor count coefficient for determining an odor sensed by the one or more odor sensors 251, 252, and 253 corresponding to a temperature, and a temperature count coefficient for the monitor sensor 254 corresponding to the temperature. In addition, the storage unit 260, under control of the controller 210, stores the signal or data that is input and/or output in response to operations of the controller 210, the communication unit 220, and the sensing unit 250. The storage unit 260 stores a control program and applications for control of the olfactory sensing device 200 or the controller 210.

The controller 210 detects a connection to the electronic device 100, the connection being made using at least one of USB, HDMI and MIPI. If an odor is sensed by the one or more odor sensors 251, 252, and 253 in the sensing unit 250, in response to a command from the electronic device 100, the controller 210 estimates the current temperature using a temperature count coefficient of the monitor sensor 254 included in the sensing unit 250. The controller 210 calculates a odor count coefficient variation for the sensor that has sensed the odor, and applies a temperature count coefficient variation, which corresponds to a temperature change, to the odor count coefficient variation, to measure the odor.

The controller 210 identifies the odor count coefficient of the sensor that has sensed the odor, and compares the identified odor count coefficient with a pre-stored odor count coefficient of the odor sensor that has sensed the odor. The controller 210 subtracts the temperature count coefficient variation, which corresponds to a temperature change, from the calculated odor count coefficient variation. The temperature change corresponds to a difference between the estimated current temperature and a reference temperature in the table. The controller 210 determines the sensed odor based on a result of the subtraction. In addition, the controller 210 updates the subtraction result in the table. The table includes an odor count coefficient for determining an odor for each of the one or more odor sensors 251, 252, and 253 corresponding to a temperature, and a temperature count coefficient for the monitor sensor 254 corresponding to the temperature. The odor count coefficient is a value obtained by converting a resonant frequency of the one or more odor sensors 251, 252, and 253, which is changed depending on the molecules of the sensed odor, into a digital value. The controller 210 converts a resonant frequency of the one or more odor sensors 251, 252, and 253 into a digital value depending on the molecules of the sensed odor. The temperature count coefficient of the monitor sensor may be pre-stored in a storage unit.

The controller 210 controls an activating or inactivating operation of the sensing unit 250 at predetermined periods of the clock output from the oscillator 240. The controller 210 estimates the current temperature using the monitor sensor 254 configured in the sensing unit 250.

The controller 210 includes a calculation module 211 for calculating an odor count coefficient variation of at the least one odor sensor that has sensed the odor, an applying module 212 for applying a temperature count coefficient variation, which corresponds to a temperature change, to the calculated odor count coefficient variation, and a determination module 213 for determining the sensed odor using the result of applying the temperature count coefficient variation to the calculated odor count coefficient variation.

The calculation module 211 identifies the odor count coefficient of the one or more odor sensors 251, 252, and 253 that has sensed the odor, and compares the identified odor count coefficient with a pre-stored odor count coefficient of the one or more odor sensors 251, 252, and 253 that has sensed the odor in a table in the storage unit 260. The calculation module 211 subtracts the temperature count coefficient variation, which corresponds to a temperature change, from the calculated odor count coefficient variation.

The applying module 212 applies the temperature count coefficient variation to the calculated odor count coefficient variation, to measure the odor.

The determination module 213 may determine the sensed odor using the result from the applying module 212. The determination module 213 may determine the sensed odor using the subtraction results.

At least one of the calculation module 211, the applying module 212 and the determination module 213 may be provided in the controller 210, or may be provided separately in the olfactory sensing device 200.

Figure 3A:
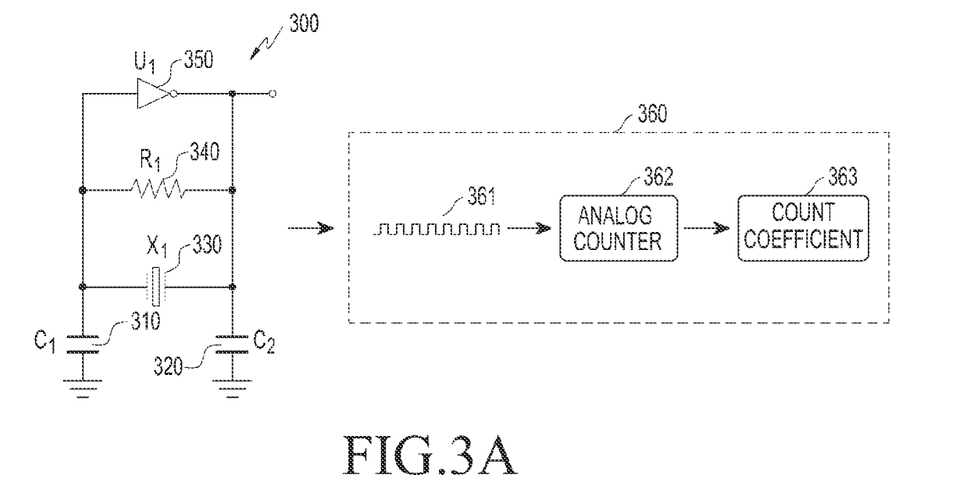
FIG. 3A illustrates a circuit of an oscillator for generating a clock to measure an odor in an olfactory sensing device, according to an embodiment of the present invention.
Figure 3B:
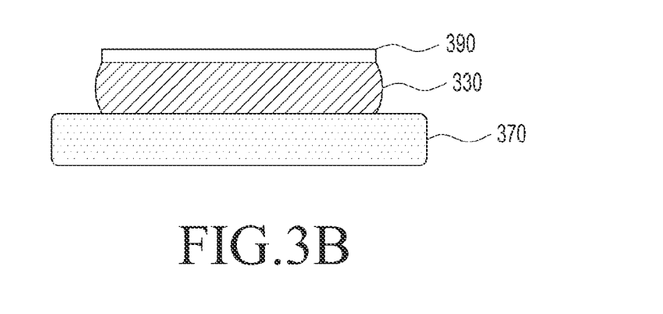
FIG. 3B illustrates a configuration of a sensor for measuring an odor in an olfactory sensing device, according to an embodiment of the present invention.

FIG. 3A illustrates a circuit of an oscillator for generating a clock to measure an odor in an olfactory sensing device, according to an embodiment of the present invention, and FIG. 3B illustrates a configuration of an odor sensor for measuring an odor in an olfactory sensing device, according to an embodiment of the present invention.

Referring to FIG. 3A, the oscillator 300 for generating a clock to measure an odor includes an inverter 350, a resistor 340, a resonator 330 and two capacitors 310 and 320. The inverter 350, the resistor 340 and the two capacitors 310 and 320 may be made by a Complementary Metal Oxide Semiconductor (CMOS) process, and the resonator 330 may be assembled by an FBAR process.

According to an embodiment of the present invention, the one or more odor sensors 251, 252, and 253 may include an FBAR sensor that is made by the FBAR process. The FBAR sensor is doped with a receptor.

When the oscillator 300 operates, the frequency output from the oscillator 300 is converted into an odor count coefficient through a count coefficient generation process 360. The output 361 of the oscillator 300 affects a value of an analog counter 362, and the analog counter 362 generates the odor count coefficient 363 by converting the received frequency value into a digital value.

Referring to FIG. 3B, the inverter 350, the resistor 340 and the two capacitors 310 and 320 in FIG. 3A may be manufactured by a CMOS process 370, and the resonator 330 may be mounted on CMOS by an FBAR process, and then doped with a receptor 390.

For example, if an odor is sensed, the resonant frequency of the FBAR is converted, so the frequency output from the oscillator 300 may also be converted. The converted frequency affects the value of the analog counter 362, and an odor is sensed or measured by using the change in the value of the analog counter 362.

Figure 4:
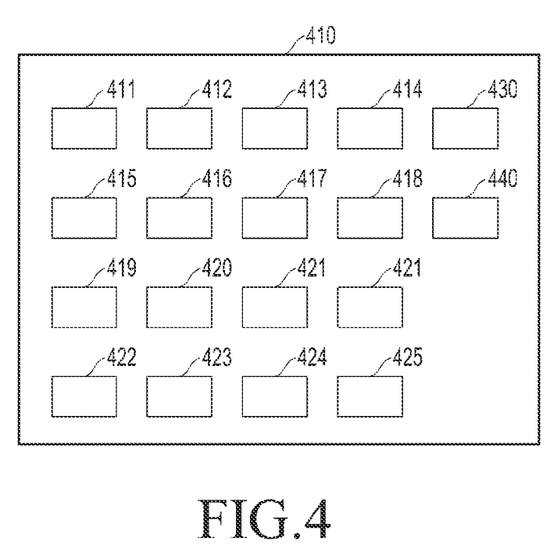
FIG. 4 illustrates an arrangement of sensors configured in a sensing unit of in an olfactory sensing device, according to an embodiment of the present invention.

FIG. 4 illustrates an arrangement of sensors configured in a sensing unit of an olfactory sensing device, according to an embodiment of the present invention.

Referring to FIG. 4, a sensing unit 410 is provided, including one or more odor sensors 411 to 425 for measuring an odor and one or more monitor sensors 430 and 440 for estimating a temperature. The at least one of the odor sensors may be an FBAR sensor.

The sensors may be configured in a single chip.

Information about an odor sensed or measured by the one or more odor sensors 411 to 425 is transmitted to the controller 210, and the controller 210 stores an odor count coefficient for the measured odor in the storage unit 260 in the form of a table. The table includes an odor count coefficient for determining an odor for each of the at least one odor sensor corresponding to a temperature, and a temperature count coefficient for the one or more monitor sensors 430 and 440 corresponding to the temperature.

The odor count coefficient is a value obtained by converting a resonant frequency of an odor sensor, which is changed depending on the molecules of the sensed odor, into a digital value. The temperature count coefficient for the monitor sensor may be pre-stored in a storage unit.

Table 1, shown below, illustrates a table showing an odor count coefficient for odor sensors, such as the one or more odor sensors 411 to 425, before odor molecules are sensed.

Table 2, shown below, illustrates a table showing an odor count coefficient for odor sensors, such as the one or more odor sensors 411 to 425, after the odor molecules are sensed.

Table 1 illustrates the result values obtained by multiple measurements, and the result values are used as reference values in measuring an odor. In addition, Table 1 is stored in advance in the storage unit 260, and is used to calculate the odor count coefficient variation of the one or more sensors 411 to 425 that has sensed an odor.

Further, Table 2 illustrates a table showing an odor count coefficient of the one or more odor sensors 411 to 425 that have sensed the odor after the odor molecules are received.

Tables 1 and 2 are used as reference values in measuring an odor. For example, when one odor sensor senses an odor molecule, an odor count coefficient variation is calculated by using Table 1 and 2. Tables 1 and 2 are illustrated as two separate pre-stored tables, however, Table 1 and 2 may be pre-stored as one table.

TABLE 1

| Odor Sensors | Odor Count Coefficients |
|---|---|
| 1 | 400,000 |
| 2 | 380,000 |
| 3 | 421,000 |
| 4 | 400,100 |
| 5 | 400,320 |

TABLE 2

| Odor Sensors | Odor Count Coefficients |
|---|---|
| 1 | 370,000 |
| 2 | 350,000 |
| 3 | 409,000 |
| 4 | 365,000 |
| 5 | 384,500 |

Each of these odor sensors has the characteristic that the frequency increases as the temperature increases. The one or more monitor sensors 430 and 440 have a temperature count coefficient corresponding to the temperature, such as shown in Table 3 below.

TABLE 3

| Sensors | 10° C. | 20° C. | 30° C. |
|---|---|---|---|
| 1 | 400,000 | 400,100 | 400,300 |
| 2 | 385,000 | 380,600 | 380,700 |
| 3 | 420,000 | 422,500 | 426,000 |
| 4 | 380,000 | 384,000 | 389,000 |
| 5 | 390,000 | 392,000 | 394,000 |
| Monitor sensor | 450,000 | 460,000 | 470,000 |

For example, as shown in Table 3, a temperature count coefficient of a monitor sensor at 10° C. is 450,000, a temperature count coefficient of a monitor sensor at 20° C. is 460,000, and a temperature count coefficient of a monitor sensor at 30° C. is 470,000.

For example, in a case where a value of an analog counter is measured as the odor molecules are received, if the temperature count coefficient of the one or more monitor sensors 430 and 440 is 470,000, the current temperature is estimated to be 30° C. In addition, it can be seen from Table 3, that in the case of a first sensor, an odor count coefficient variation (e.g., frequency change) increases by 300 at a temperature of 30° C. compared with the reference temperature (e.g., 10° C.). It can be seen from Tables 1 and 2 that a first sensor's odor count coefficient variation by the odor molecules is 400,000−370,000=30,000. If the odor count coefficient variation by the odor molecules (i.e. 30,000) is adjusted by the temperature count coefficient variation (i.e., 300), the actual net change by the odor molecules is 29,700. Based on this result value of 29,700, the sensed odor is determined.

The one or more monitor sensors 430 and 440 may be provided outside the olfactory sensing device 200. In addition, the one or more monitor sensors 430 and 440 may be disposed in the position where the monitor sensors 430 and 440 can measure the ambient temperature.

Figure 5:
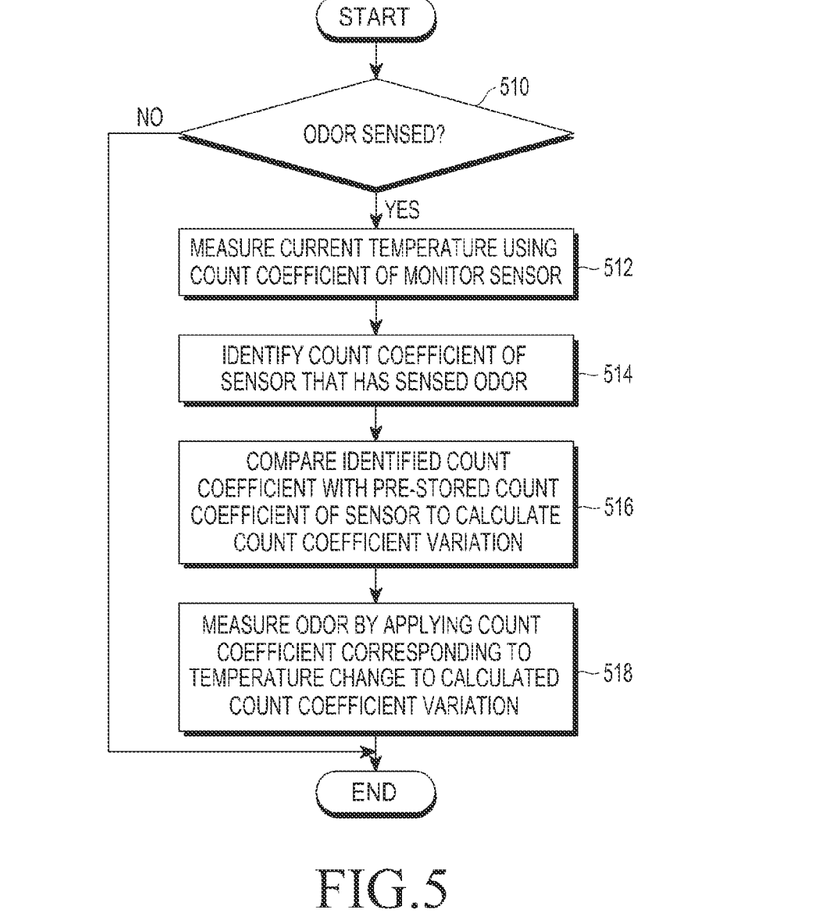
FIG. 5 is a flowchart illustrating a method for measuring an odor in an olfactory sensing device, according to an embodiment of the present invention.

FIG. 5 is a flowchart illustrating a method for measuring an odor in an olfactory sensing device, according to an embodiment of the present invention.

Referring to FIG. 5, a method for measuring an odor in an olfactory sensing device 200 is provided.

If an odor is sensed in step 510 by the one or more odor sensors 251, 252, and 253 of the olfactory sensing device 200, the olfactory sensing device 200 estimates the current temperature using the temperature count coefficient of the monitor sensor in step 512. The olfactory sensing device 200 estimates the current temperature using the monitor sensor 254 configured in the sensing unit 250.

In step 515, the olfactory sensing device 200 identifies an odor count coefficient of the one or more odor sensors 251, 252, and 253 that has sensed the odor.

In step 516, the olfactory sensing device 200 compares the identified odor count coefficient with a pre-stored odor count coefficient of the one or more odor sensors 251, 252, and 253 which sensed the odor, to calculate an odor count coefficient variation. The olfactory sensing device 200 calculates an odor count coefficient variation of the one or more odor sensors 251, 252, and 253 that has sensed the odor. This calculation includes identifying an odor count coefficient of the one or more odor sensors 251, 252, and 253 that has sensed the odor, and comparing the identified odor count coefficient with a pre-stored odor count coefficient of the one or more sensors 251, 252, and 253 that has sensed the odor. The pre-stored odor count coefficient is stored in a table. Also, the table may include an odor count coefficient for each of the one or more odor sensors 251, 252, and 253 corresponding to a temperature, and a temperature count coefficient of the monitor sensor 254, corresponding to the temperature.

The odor count coefficient is a value obtained by converting a resonant frequency of the odor sensor, which is changed depending on the molecules of the sensed odor, into a digital value.

In step 518, the olfactory sensing device 200 measures the odor by applying a temperature count coefficient variation, which corresponds to the temperature change, to the calculated odor count coefficient variation. The odor is measured by subtracting the temperature count coefficient variation from the calculated odor count coefficient variation. The temperature change corresponds to a difference between the estimated current temperature and a reference temperature (e.g., 10° C.) stored in the table. In addition, the olfactory sensing device 300 determines the sensed odor based on the result of the subtraction. Further, the olfactory sensing device updates the subtraction result in the table.

As is apparent from the foregoing description, the olfactory sensing device, according to various embodiments of the present invention, measures an odor by correcting for a change in temperature, without a separate device for measuring the temperature, making it possible to reduce the cost and size of the product.

The term 'module' used in the present disclosure may refer to a unit that includes any one of, for example, hardware, software or firmware, or a combination of two or more of them. The 'module' may be interchangeably used with terms, such as unit, logic, logical block, component or circuit. The 'module' may be the minimum unit of unitized parts, or a part thereof. The 'module' may be the minimum unit for performing one or more functions, or a part thereof. The 'module' may be implemented mechanically or electronically. For example, the 'module', according to an embodiment of the present invention, may include at least one of an Application-Specific Integrated Circuit (ASIC) chip, Field-Programmable Gate Arrays (FPGAs), or a programmable-logic device for performing certain operations, which is now known or will be developed in the future.

According to various embodiments of the present invention, at least some of the device (e.g., modules or functions thereof) or methods (e.g., operations) may be implemented by a command that is stored in computer-readable storage media in the form of, for example, a programming module. If the command is executed by one or more processors (e.g., the controller 210), the one or more processors performs the function corresponding to the command. The computer-readable storage media may be, for example, the storage unit 260. At least a portion of the programming module may be implemented (or executed) by, for example, the controller 210. The at least a portion of the programming module may include, for example, a module, a program, a routine, a set of instructions, or a process for performing one or more functions.

The computer-readable storage media may include magnetic media (e.g., hard disk, floppy disk, magnetic tape and the like), optical media (e.g., Compact Disc Read Only Memory (CD-ROM), DVD and the like), magneto-optical media (e.g., floptical disk and the like), and a hardware device (e.g., Read Only Memory (ROM), Random Access Memory (RAM), flash memory and the like) that is specially configured to store and perform a program command (e.g., a programming module).

The program command may include, not only the machine code produced by a compiler, but also the high-level language code that can be executed by the computer using an interpreter and the like.

The above-described hardware device may be configured to operate as one or more software modules to perform the operation according to the present invention, and vice versa.

The module or programming module according to the present invention may include at least one or more of the above-described components, some of which may be omitted, or may further include additional other components. The operations that are performed by the module, programming module, or other components may be executed in a sequential, parallel, iterative, or heuristic manner. In addition, some operations may be executed in a different order, or may be omitted, or other operations may be added.

According to various embodiments of the present invention, there may be a storage media storing instructions, the instructions, when executed by at least one processor, may be set to allow the at least one processor to perform at least one operation of the various methods described herein.

While the invention has been shown and described with reference to certain embodiments described herein, it will be understood by those skilled in the art that various changes in form and details may be made therein without departing from the spirit and scope of the invention as defined by the appended claims and their equivalents.

What is claimed is:

1. A method for measuring an odor in an electronic device including a memory, a processor, a display and a sensing unit which includes a plurality of odor sensors and at least one monitor sensor, the method comprising:
    sensing, by one or more of the plurality of odor sensors, an odor around the electronic device;
    obtaining, by the processor, a first odor count value for an odor sensor that has sensed the odor among the plurality of odor sensors;
    obtaining, by the processor, a first odor count value variation by subtracting the obtained first odor count value from a pre-stored second odor count value of the odor sensor prior to sensing the odor, wherein the pre-stored second odor count value is stored in a first table of the memory;
    obtaining, by the processor, a temperature count value from the at least one monitor sensor;
    estimating, by the processor, a current temperature around the electronic device based on the obtained temperature count value;
    obtaining, by the processor, a first temperature count value for the odor sensor corresponding to the current temperature by using the obtained temperature count value;
    obtaining, by the processor, a second odor count value variation by subtracting a second temperature count value for the odor sensor corresponding to a reference temperature from the obtained first temperature count value, the second temperature count value being stored in a second table of the memory;
    identifying, by the processor, a level of the sensed odor around the electronic device by subtracting the second odor count value variation from the first odor count value variation; and
    displaying, on the display, the identified level of the sensed odor.

2. The method of claim 1, further comprising updating, by the processor, a result of the subtraction into the second table.

3. The method of claim 1, wherein the second table includes the odor count value for each of the plurality of odor sensors corresponding to one or more temperatures, and the temperature count value for each of the at least one monitor sensor corresponding to the at least one or more temperatures.

4. The method of claim 1, wherein each of the first odor count value and the second odor count value is obtained by converting a resonant frequency of the odor sensor, which is changed depending on molecules of a sensed odor, into a digital value.

* * * * *